United States Patent [19]

Yueh et al.

[11] 4,418,080

[45] Nov. 29, 1983

[54] NATURAL RED COLORING PREPARED FROM WHEAT AND BARLEY SUBSTRATES

[75] Inventors: Mao Yueh, Barrington; Stephan A. Rashbaum, Evanston, both of Ill.

[73] Assignee: The Quaker Oats Company, Chicago, Ill.

[21] Appl. No.: 280,618

[22] Filed: Jul. 6, 1981

[51] Int. Cl.$^3$ .......................... A23L 1/27; A23L 1/28; C12P 1/02; C12N 1/14

[52] U.S. Cl. ..................... 426/18; 426/250; 426/270; 435/171; 435/254; 435/911

[58] Field of Search .................. 426/250, 270, 18, 44; 435/254, 171, 911

[56] References Cited

U.S. PATENT DOCUMENTS

| | | | |
|---|---|---|---|
| 3,243,301 | 3/1966 | Hesseltine et al. ..................... | 426/18 |
| 3,615,674 | 10/1971 | Bass et al. ............................. | 426/250 |
| 3,765,906 | 10/1973 | Yamaguchi et al. .................. | 99/148 |
| 3,885,048 | 5/1975 | Liggett .................................. | 426/18 |
| 3,911,141 | 10/1975 | Farr et al. ............................ | 426/60 |
| 4,031,250 | 6/1977 | Haas et al. ............................ | 426/18 |
| 4,145,254 | 3/1979 | Shepherd et al. .................... | 426/250 |

FOREIGN PATENT DOCUMENTS 498123  12/1953  Canada ................................ 426/250

*Primary Examiner*—Raymond N. Jones
*Assistant Examiner*—Elizabeth J. Curtin
*Attorney, Agent, or Firm*—Karen E. Ayd; G. T. Shekleton; J. P. O'Halloran

[57] ABSTRACT

A food product is prepared having a red-meaty color imparted thereto by the incorporation of an effective amount of pigments produced by the growth of the mold of the genus Monascus on both wheat substrates and barley substrates.

5 Claims, No Drawings

NATURAL RED COLORING PREPARED FROM WHEAT AND BARLEY SUBSTRATES

BACKGROUND OF THE INVENTION

This invention relates to food products and more particularly to the coloring of such food products to obtain a meaty-red color.

Food colorant agents for meats, whether they be for human or pet foods, are generally formulated to give the appearance of real meat in both color and texture. Use of the pigments produced by the growth of the mold Monascus purpureus on material selected from rice and corn has been taught for use as food coloring when added to food products by U.S. Pat. Nos. 3,911,141, 4,031,250, and 4,145,254 and others. Such treated rice or corn is generally subdivided and used per se as the coloring material. The corn or rice thereby serves both as a nutrient source as well as a colorant in the food.

To date there have been no teachings that molds of the genus Monascus, such as Monascus purpureus and Monascus anker could be successfully cultivated on either wheat or barley substrates and thereby take advantage of such grains' excellent, nutritive and other helpful qualities. In addition, it is known that whole grain wheat or barley will not uniformly or efficiently support the growth of molds of the genus Monascus in known mediums in the same manner as will other grains, such as rice and corn. As a result, there have been no published successful attempts to cultivate molds of the genus Monascus on wheat or barley, even though rice or corn have each been used successfully as substrates.

SUMMARY OF THE INVENTION

It is therefore an object of the subject invention to produce a red color through the fermentation of molds of the genus Monascus on a substrate of wheat or barley.

It is another object of the subject invention to provide a red-meaty color in food products through the incorporation of pigments produced by the growth of molds of the genus Monascus on a solid or liquid substrate of wheat or barley.

A further object of the subject invention is an improved process for the production of a red color on a substrate such as wheat or barley in a fast and efficient manner.

These and other objects are attained in accordance with the present invention wherein there is provided pigments produced by the growth of molds of the genus Monascus on materials selected from either steel cut and tempered wheat, wheat flour, pearled barley or barley flour; such treated material can be used directly as a food coloring agent for supplying a meaty-red color to the food product. The pigments produced through the method of the subject invention stain the grain substrate which may be dried, ground, and utilized as an integral part of the fool product being colored. For instance, in pet foods the stained grain may be used as a direct replacement for the grain content of the pet food. As stated, the substrate used in the culturing of molds of the genus Monascus may be either a solid substrate utilizing steel cut grain or a liquid substrate utilizing an aqueous nutrient medium and steel cut grain or grain flour under aerobic conditions. In addition a greatly reduced fermentation time is gained over the methods of the prior art, while still yielding color of the intensity desired.

DETAILED DESCRIPTION OF THE INVENTION

Further objects of the invention together with additional features contributing thereto and advantages accruing therefrom will be apparent from the following description of several embodiments of the invention.

A strain of a microorganism of the genus Monascus which produces pigment of the monascorubrin or rubropunctatin type may be used for carrying out the process according to the subject invention. An inoculum of the strain selected may be prepared from a reconstituted, freeze dried culture, or from a culture on a solid or liquid medium by any method known in the art.

In general the method of the subject invention involves preparing the grain substrate to be inoculated in a moist or aqueous fashion. This grain substrate is sterilized by moist heat to temperatures above 100° C. In a preferred embodiment of the subject invention, a simple autoclave process with temperatures typically in excess of 100° C., and generally 121° C. at 15 psi pressure for about 15 minutes, or, a period of time sufficient to kill any viable microorganism and to gelatinize any starch contained within the substrate so as to make it available to molds of the genus Monascus, is used. The substrate contained in the sterile vessel is then inoculated with the Monascus mold so that the viable organism is evenly distributed throughout the growth medium and then allowed to ferment unhindered until completion of its growth cycle, as monitored by the completion of coloration of the substrate. The moisture level is maintained at approximately 30% throughout the growth cycle of the organism by addition of water as necessary. The colored grain substrate may then be dried, ground, and utilized as a food colorant.

When a liquid substrate is preferred, an aqueous, nutritious solution must first be prepared such as through the mixture of magnesium sulfate, sodium nitrate, and potassium phosphate and blending this nutrient solution with the wheat or barley flour as desired. For maximum color levels, the concentration of the nutrient solution should be such as to permit optimum growth of the mold on the substrate, as known in the art. From a practical viewpoint, the salt concentration must be higher if more grain is included as substrate. The nutrient solution may include amino acids, sugars, starches, protein hydrolysates, molasses, casein, yeast extracts and other ingredients as known in the art. The grain-nutrient solution is then sterilized, such as through autoclaving as stated above, and cooled. The resulting sterilized grain-nutrient solution is placed in a glass flask, inoculated, and aerated by continuous shaking at intermediate speeds until the growth cycle of the Monascus mold is complete. Such shaking speeds up the growth of the mold as well as pigmentation of the substrate. The resulting colored substrate may be collected by centrifugation, drying, and grinding to a desired particle size. Colored substrate may then be used through addition to food products as desired.

The invention is better illustrated through reference to the following examples:

EXAMPLE I

Hard red winter wheat was cut so that each individual piece of grain would be fractured into no more than three pieces. 50 grams of this wheat substrate was immersed in excess water for 5 minutes after which time the excess water was removed by draining through cheesecloth and squeezing in cheesecloth bag. The moistened wheat grains were placed in a 500 ml flask and sterilized by autoclaving at 121° C. for 15 minutes. The sterile vessel was inoculated with *Monascus purpureus* from a water washed slant and incubated at 25° C. until the maximum amount of coloration had appeared—approximately 3 weeks. Throughout the incubation period, water was added as necessary to maintain the moisture content of the grain, around 30%. After the incubation period, the cultured wheat grain was harvested and examined. The cultured grain was found to be a rich red on the surface and with the same color extending down past the surface of the particle grain extending through the entire interior of each piece of grain. The color was evenly distributed throughout the entire culture and most suitable for future use, such as by inclusion in a pet food as a direct substitute for the grain content of the pet food.

EXAMPLE II

Food colorants were prepared through the fermentation of *Monascus purpureus* with hard red winter wheat in a submerged nutrient culture. The nutrient culture comprises a suitable salt-supplemented solution, the salts being chosen to provide both buffering capacity and essential mineral nutrients for the growth of the organism. 10 grams of fractured hard red winter wheat were added to a 500 ml flask containing 100 ml water having 0.2% $MgSO_4.7H_2O$, 0.3% $NaNO_3$ and 0.5% $KH_2PO_4$. After sterilization and inoculation, either from a water washed slant or previously grown liquid culture, the flask was placed on a platform shaker and incubated at 25° to 30° C. with agitation sufficient to supply adequate aeration, typically 225 rpm, for approximately 48 hours, at which time the coloration of the substrate was complete. The colored substrate was collected by centrifugation, and dried prior to use, typically by freeze drying or air drying.

EXAMPLE III

In a manner similar to that in Example 2, wheat flour was added to a solution containing 0.2% $MgSO_4.7H_2O$, 0.3% $NaNO_3$, and 0.5% $KH_2PO_4$, typically 10 grams into 100 ml solutions in a 500 ml flask. After sterilization and inoculation, as above, the solution was shaken to provide aeration, typically 225 rpm at 25° C. The colored substrate was produced under these conditions typically in 48 hours. The material was harvested and dried as in Example 2.

EXAMPLE IV

In a manner similar to that of Example II, 50 g of pearled barley was tempered, sterilized and inoculated. Inoculation with aeration of the inoculated barley substrate yielded an excellently colored grain after 48 hours. The material was harvested and dried as in Example II.

EXAMPLE V

The dried colored substrate prepared as in Examples I, II, III and IV was each milled to a consistency similar to that of flour. This powdered material was found to be effective in imparting a meatlike color to both human and pet foods. Concentration varied from 0.05% to 5.0% depending upon the formulation of the pet food and the color intensity desired.

In each of the examples set forth above it was noted that, in a dog food product, commonly termed burger, which has been colored with the *Monascus purpureus* cultured wheat or barley, little or no permanent discoloration of either nylon or wool carpeting was observed when treated with a mixture of burger and simulated gastric juice (0.5% HCl, 5 mg/ml pepsin and 1 mg/ml lipase). In other words the initial, color stain was easily removed with standard cleaning solution. Commercially available burger, colored with FD+C Red #40 or Aluminum Red #40 Lake, when mixed with the simulated gastric juice and applied to the carpeting left prominent stains that were not removable by standard techniques.

While the invention has been described with reference to a preferred embodiment, it will be understood by those skilled in the art that various changes may be made and equivalents may be substituted for elements thereof without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A method for imparting a red, meaty color to a food product comprising culturing a mold of the genus Monascus on a grain substrate selected from the group of wheat and barley, to obtain red pigments thereon, wherein the step of culturing the Monascus mold comprises:
   a. preparing a nutrient solution by mixing water with a salt selected from the group consisting of $MgSO_4$, $KH_2PO_4$, $NaNO_3$;
   b. submerging a grain substrate selected from the group of barley and wheat grain flour or steel cut grain in the nutrient solution to form a grain and nutrient solution;
   c. inoculating said grain and nutrient solution with *Monascus purpureus* mold;
   d. agitating the mold-inoculated grain and nutrient solution to aerate;
   e. incubating the *Monascus purpureus* mold in the agitated grain and nutrient solution, yielding a red pigmented grain product; and
   f. adding the red pigmented grain product as an ingredient to a food product.

2. The method of claim 1 wherein the salt in the nutrient solution is in an amount of 0.2% to 0.5% based on the water.

3. The method of claim 1 wherein the wheat or barley grain substrate is in an amount approximately 10% based on the weight of the water.

4. The method of claim 1 wherein the wheat or barley substrate is sterilized prior to addition to the nutrient solution.

5. The method of claim 1 wherein the incubation temperature is in the range of about 25° to 30° C., inclusive.

* * * * *